(12) United States Patent
Zhang et al.

(10) Patent No.: US 11,107,212 B2
(45) Date of Patent: Aug. 31, 2021

(54) METHODS AND SYSTEMS FOR DISPLAYING A REGION OF INTEREST OF A MEDICAL IMAGE

(71) Applicant: SHANGHAI UNITED IMAGING INTELLIGENCE CO., LTD., Shanghai (CN)

(72) Inventors: Jianfeng Zhang, Shanghai (CN); Yanli Song, Shanghai (CN); Dijia Wu, Shanghai (CN); Yiqiang Zhan, Shanghai (CN); Xiang Sean Zhou, Shanghai (CN)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 0 days.

(21) Appl. No.: 16/421,017

(22) Filed: May 23, 2019

(65) Prior Publication Data

US 2020/0273160 A1    Aug. 27, 2020

(30) Foreign Application Priority Data

Feb. 22, 2019    (CN) .......................... 201910133231.2

(51) Int. Cl.
*G06T 15/08*    (2011.01)
*G06T 7/00*    (2017.01)
(Continued)

(52) U.S. Cl.
CPC .............. *G06T 7/0012* (2013.01); *G06T 7/11* (2017.01); *G06T 7/136* (2017.01); *G06T 15/08* (2013.01);
(Continued)

(58) Field of Classification Search
CPC ..................... G06T 7/0012; G06T 7/11; G06T 2207/10081; G06K 2209/05; G06K 9/00744
See application file for complete search history.

(56) References Cited

U.S. PATENT DOCUMENTS

2018/0314691 A1*    11/2018    Mori ..................... G06T 7/0014

FOREIGN PATENT DOCUMENTS

| CN | 102187368 A | 9/2011 |
|---|---|---|
| CN | 102938013 A | 2/2013 |

(Continued)

OTHER PUBLICATIONS

Chinese Patent Office, Office Action dated Sep. 29, 2019, in Application No. 201910133231.2.
(Continued)

*Primary Examiner* — Sam Bhattacharya
(74) *Attorney, Agent, or Firm* — Faegre Drinker Biddle & Reath LLP

(57) ABSTRACT

Method and system for displaying one or more regions of interest of an original image. For example, a computer-implemented method for displaying one or more regions of interest of an original image includes: obtaining one or more detection results of one or more first regions of interest, each detection result of the one or more detection results corresponding to one first region of interest of the one or more first regions of interest, each detection result including image information and one or more attribute parameters for their corresponding first region of interest; and obtaining one or more attribute parameter thresholds provided by a user in real time, each attribute parameter threshold of the one or more attribute parameter thresholds corresponding to one attribute parameter of the one or more attribute parameters.

15 Claims, 10 Drawing Sheets

(51) Int. Cl.
*G16H 50/20* (2018.01)
*G06T 7/11* (2017.01)
*G06T 7/136* (2017.01)
*G16H 30/40* (2018.01)
*A61B 6/00* (2006.01)
*G16H 50/70* (2018.01)
*G06T 11/00* (2006.01)
*A61B 5/055* (2006.01)
*A61B 6/03* (2006.01)

(52) U.S. Cl.
CPC ............. *G16H 30/40* (2018.01); *G16H 50/20* (2018.01); *A61B 5/055* (2013.01); *A61B 6/032* (2013.01); *A61B 6/469* (2013.01); *G06T 11/005* (2013.01); *G06T 2207/10072* (2013.01); *G06T 2207/10132* (2013.01); *G06T 2207/30004* (2013.01); *G06T 2210/41* (2013.01); *G16H 50/70* (2018.01)

(56) References Cited

FOREIGN PATENT DOCUMENTS

| | | |
|---|---|---|
| CN | 103610473 A | 3/2014 |
| CN | 104809717 A | 7/2015 |
| CN | 106649332 A | 5/2017 |
| CN | 106709929 A | 5/2017 |
| CN | 106940816 A | 7/2017 |
| CN | 107358053 A | 11/2017 |
| CN | 107392893 A | 11/2017 |
| CN | 107544736 A | 1/2018 |
| CN | 107578402 A | 1/2018 |
| CN | 108664181 A | 10/2018 |
| CN | 108961296 A | 12/2018 |
| CN | 109035283 A | 12/2018 |

OTHER PUBLICATIONS

Chinese Patent Office, Office Action dated Dec. 31, 2019, in Application No. 201910133231.2.
Chinese Patent Office, Office Action dated Apr. 15, 2020, in Application No. 201910133231.2.
Chinese Patent Office, Office Action dated Aug. 7, 2020, in Application No. 201910133231.2.
Chinese Patent Office, Office Action dated Mar. 1, 2021, in Application No. 201910133231.2.
Chinese Patent Office, Office Action dated Jun. 22, 2021, in Application No. 201910133231.2.
Gao et al., selected pages from *Radiological [Radiological] Anatomy and Diagnosis Atlas of General Surgery*, Guangdong Science and Technology Publishing House, 2013 (as included with the Chinese Office Action dated Jun. 22, 2021, in connection with Application No. 201910133231.2).

* cited by examiner

METHODS AND SYSTEMS FOR DISPLAYING A REGION OF INTEREST OF A MEDICAL IMAGE

1. CROSS-REFERENCES TO RELATED APPLICATIONS

This application claims priority to Chinese Patent Application No. 201910133231.2, filed Feb. 22, 2019, incorporated by reference herein for all purposes.

2. BACKGROUND OF THE INVENTION

Certain embodiments of the present invention are directed to image processing. More particularly, some embodiments of the invention provide methods and systems for displaying a region of interest of a medical image. Merely by way of example, some embodiments of the invention have been applied to diagnosing a medical image. But it would be recognized that the invention has a much broader range of applicability.

In recent years, with the rapid development of deep learning technology, Computer Aided Diagnosis (CAD) systems based on artificial intelligence has been increasingly used in identifying and segmenting or detecting feature parts in medical images, greatly reducing the burden of doctor analysis of medical images. However, due to the limitations of training data, the inherent bottleneck of the algorithm itself, and the diversity and uncertainty of the feature parts themselves, there are still certain proportion of false positive results in existing computer-aided diagnosis systems. The area of the feature portion is predicted as a feature portion.

A method used in the art pertains weighing the relationship between the detection rate and the false positive rate by drawing a Receiver Operating Characteristic Curve (ROC curve), and a suitable parameter threshold is generally selected based on the ROC curve as the actual use computer. An auxiliary diagnostic system performs the threshold for screening test results. However, once the parameter threshold is selected, the doctor cannot use different parameter thresholds to balance the detection rate with different use scenarios and different case characteristics when using the computer-aided diagnosis system. The false positive rate, which cannot achieve different degrees of balance between diagnostic accuracy and reading time, reduces the versatility of computer-aided diagnostic systems.

3. BRIEF SUMMARY OF THE INVENTION

Certain embodiments of the present invention are directed to image processing. More particularly, some embodiments of the invention provide methods and systems for displaying a region of interest of a medical image. Merely by way of example, some embodiments of the invention have been applied to diagnosing a medical image. But it would be recognized that the invention has a much broader range of applicability.

In various embodiments, a computer-implemented method for displaying one or more regions of interest of an original image includes obtaining one or more detection results of one or more first regions of interest. In some examples, each detection result of the one or more detection results corresponding to one first region of interest of the one or more first regions of interest. In certain examples, each detection result includes image information and one or more attribute parameters for their corresponding first region of interest. In various examples, the method further includes obtaining one or more attribute parameter thresholds provided by a user in real time. In some examples, each attribute parameter threshold of the one or more attribute parameter thresholds corresponds to one attribute parameter of the one or more attribute parameters. In various examples, the method includes obtaining one or more second regions of interest from the one or more first regions of interest based on at least comparing the one or more attribute parameters with the one or more attribute parameter thresholds respectively. In various examples, the method includes displaying image information corresponding to each second region of interest of the one or more second regions of interest.

In some embodiments, the one or more attribute parameters include at least one selected from a group consisting of confidence level, category, and size.

In some embodiments, the obtaining one or more attribute parameter thresholds input by a user in real time includes obtaining one or more control information of a threshold control component in response to operation of the threshold control component by the user and determining the one or more attribute parameter thresholds based on at least one or more predetermined mapping relationships between the one or more control information and the one or more attribute parameter thresholds.

In some embodiments, the displaying image information corresponding to each second region of interest of the one or more second regions of interest includes obtaining one or more partial images from the original image, each of the one or more partial images corresponding to one second region of interest of the one or more second regions, rendering the one or more partial images, and displaying the rendered one or more partial images.

In some embodiments, the image information corresponding to each second region of interest of the one or more second regions of interest includes at least one selected from a group consisting of location and size and wherein displaying image information corresponding to each second region of interest of the one or more second regions of interest includes obtaining the original image, obtaining the one or more second regions of interest from the original image based on at least the image information corresponding to each second region of interest, and displaying one or more partial images from the original image, each of the one or more partial images corresponding to one second region of interest of the one or more second regions.

In some embodiments, displaying image information corresponding to each second region of interest of the one or more second regions of interest includes generating one or more target indices corresponding to image information corresponding to the one or more second regions of interest respectively and displaying the one or more target indices.

In some embodiments, the computer-implemented method further includes receiving a selection signal for one target index of the one or more target indices; selecting one second region of interest of the one or more second regions of interest based on at least its corresponding image information corresponding to the selected one target index; and labeling at least one of: one of the one or more partial images from the original image corresponding to the selected one target index; and one of the rendered one or more partial images corresponding to the selected one target index.

In some embodiments, the one or more first regions of interest includes an anatomical structure or a lesion.

In various embodiments, a device for displaying a point of interest of an original image includes: a first module configured to obtain one or more detection results of one or more first regions of interest, each detection result of the one or more detection results corresponding to one first region of interest of the one or more first regions of interest, each detection result including image information and one or more attribute parameters for their corresponding first region of interest; a second module configured to obtain one or more attribute parameter thresholds provided by a user in real time, each attribute parameter threshold of the one or more attribute parameter thresholds corresponding to one attribute parameter of the one or more attribute parameters; a third module configured to obtain one or more second regions of interest from the one or more first regions of interest based on at least comparing the one or more attribute parameters with the one or more attribute parameter thresholds respectively; and a displaying module configured to display image information corresponding to each second region of interest of the one or more second regions of interest.

In some embodiments, the one or more attribute parameters include at least one selected from a group consisting of confidence level, category, and size.

In some embodiments, the second module is configured to: obtain one or more control information of a threshold control component in response to operation of the threshold control component by the user; and determine the one or more attribute parameter thresholds based on at least one or more predetermined mapping relationships between the one or more control information and the one or more attribute parameter thresholds.

In some embodiments, the displaying module is configured to: obtain one or more partial images from the original image, each of the one or more partial images corresponding to one second region of interest of the one or more second regions; render the one or more partial images; and display the rendered one or more partial images.

In some embodiments, the second information corresponds to the one or more target points of interest includes at least one of location and size, and the displaying module is configured to: obtain the original image; obtain the one or more second regions of interest from the original image based on at least the image information corresponding to each second region of interest; and display one or more partial images from the original image, each of the one or more partial images corresponding to one second region of interest of the one or more second regions.

In some embodiments, the displaying module is configured to: generate one or more target indices corresponding to image information corresponding to the one or more second regions of interest respectively; and display the one or more target indices.

In various embodiments, a non-transitory computer-readable medium with instructions stored thereon, that when executed by a processor, perform the processes including: obtaining one or more detection results of one or more first regions of interest, each detection result of the one or more detection results corresponding to one first region of interest of the one or more first regions of interest, each detection result including image information and one or more attribute parameters for their corresponding first region of interest; obtaining one or more attribute parameter thresholds provided by a user in real time, each attribute parameter threshold of the one or more attribute parameter thresholds corresponding to one attribute parameter of the one or more attribute parameters; obtaining one or more second regions of interest from the one or more first regions of interest based on at least comparing the one or more attribute parameters with the one or more attribute parameter thresholds respectively; and displaying image information corresponding to each second region of interest of the one or more second regions of interest.

In some embodiments, the one or more attribute parameters include at least one selected from a group consisting of confidence level, category, and size.

In some embodiments, the non-transitory computer-readable medium, when executed by the processor, perform the processes including: obtaining one or more control information of a threshold control component in response to operation of the threshold control component by the user; and determining the one or more attribute parameter thresholds based on at least one or more predetermined mapping relationships between the one or more control information and the one or more attribute parameter thresholds.

In some embodiments, the non-transitory computer-readable medium, when executed by the processor, perform the processes including: obtaining one or more partial images from the original image, each of the one or more partial images corresponding to one second region of interest of the one or more second regions; rendering the one or more partial images; and displaying the rendered one or more partial images.

In some embodiments, the non-transitory computer-readable medium, wherein the image information corresponding to each second region of interest of the one or more second regions of interest includes at least one selected from a group consisting of location and size; and wherein when executed by the processor, perform the processes including: obtaining the original image; obtaining the one or more second regions of interest from the original image based on at least the image information corresponding to each second region of interest; and displaying one or more partial images from the original image, each of the one or more partial images corresponding to one second region of interest of the one or more second regions.

In some embodiments, the non-transitory computer-readable medium, when executed by the processor, perform the processes including: generating one or more target indices corresponding to image information corresponding to the one or more second regions of interest respectively; and displaying the one or more target indices.

4. BRIEF DESCRIPTION OF THE DRAWINGS

5. DETAILED DESCRIPTION OF THE INVENTION

Figure 1:
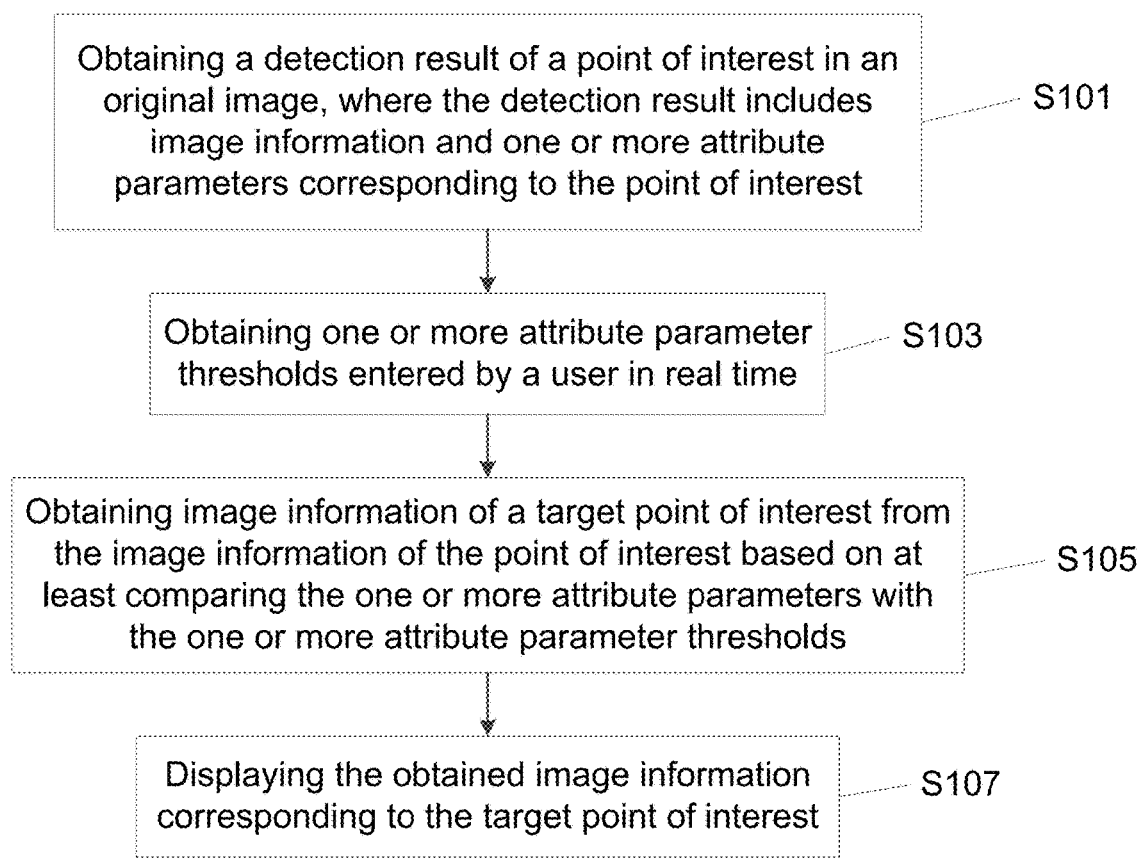
FIG. 1 is a simplified diagram showing a method for displaying a point of interest of an image, according to some embodiments of the present invention.

Certain embodiments of the present invention are directed to image processing. More particularly, some embodiments of the invention provide methods and systems for displaying a region of interest of a medical image. Merely by way of example, some embodiments of the invention have been applied to diagnosing a medical image. But it would be recognized that the invention has a much broader range of applicability.

According to some embodiments, a method, a device and a terminal for displaying a point of interest in an image (e.g., a medical image) are disclosed. In various embodiment, a method includes: obtaining a detection result (e.g., one or more detection results) of a point of interest (e.g., first point of interest) in an image (e.g., a medical image, such as an original image), where the detection result includes image information (e.g., first image information) and one or more attribute parameters corresponding to the point of interest; obtaining one or more attribute parameter thresholds entered by a user (e.g., in real time); obtaining image information (e.g., second image information) of a target point of interest (e.g., second point of interest) from the image information of the point of interest based on at least comparing the one or more attribute parameters with the one or more attribute parameter thresholds; and displaying the obtained image information corresponding to the target point of interest. The disclosed method, device and/or terminal for displaying a point of interest in an image can enable a user to adjust one or more attribute parameter thresholds, such as in real time, such that the detection result satisfying (e.g., being under) the one or more attribute thresholds are displayed (e.g., in real time). This can be beneficial for the user to weigh different degrees of balance between diagnosis accuracy and read time, for use in various usage scenarios and case characteristics, thus increasing the versatility of computer-aided diagnostic systems.

In various embodiment, a method includes obtaining a detection result (e.g., one or more detection results) of a point of interest (e.g., first point of interest) in an image (e.g., a medical image, such as an original image), where the detection result includes image information (e.g., first image information) and one or more attribute parameters corresponding to the point of interest; obtaining one or more attribute parameter thresholds entered by a user (e.g., in real time); obtaining image information (e.g., second image information) of a target point of interest (e.g., second point of interest) from the image information of the point of interest based on at least comparing the one or more attribute parameters with the one or more attribute parameter thresholds; and displaying the obtained image information corresponding to the target point of interest.

In some embodiments, the one or more attribute parameters include at least one selected from a group consisting of confidence level, category, and size.

In some embodiments, the obtaining one or more attribute parameter thresholds input by a user (e.g., in real time) includes obtaining control information (e.g., one or more control information) of a threshold control component in response to operation of the threshold control component by the user (e.g., in real time) and determining the one or more attribute parameter thresholds based on at least one or more predetermined mapping relationships between the control information and the one or more attribute parameter thresholds.

In some embodiments, the displaying the obtained image information corresponding to the target point of interest includes obtaining a partial image (e.g., one or more partial images) corresponding to the target point of interest from the image, rendering the partial image, and displaying the rendered partial image.

In some embodiments, the image information corresponding to the target point of interest includes location and/or size. In some examples, displaying image information corresponding to the target point of interest includes obtaining the original image, determining a target region of interest corresponding to the target point of interest in the original image based on at least location information and size information of the target point of interest, and displaying the original image including the target region of interest.

In some embodiments, displaying image information corresponding to the target point of interest includes generating a target index corresponding to the image information corresponding to the image information of the target point of interest and displaying the target index.

In some embodiments, the method further includes receiving a selection signal for a target index; determining image information of the target point of interest based on at least the selection signal; and labeling image information of the target point of interest corresponding to the target point of interest in the original image and/or labeling the rendered partial image corresponding to the information of the target point of interest.

In some embodiments, the target point of interest includes an anatomical structure or a lesion.

In various embodiments, a device for displaying a point of interest of an image (e.g., an original image) includes: a first obtaining module configured to obtain a detection result (e.g., one or more detection results) of a point of interest (e.g., first point of interest) in the image (e.g., a medical image, such as an original image), where the detection result includes image information and one or more attribute parameters; a second obtaining module configured to obtain one or more attribute parameter thresholds entered by a user (e.g., in real time); a third obtaining module configured to obtain image information (e.g., second image information) of a target point of interest (e.g., second point of interest) from the image information of the point of interest based on at least comparing the one or more attribute parameters with the one or more attribute parameter thresholds; and a displaying module configured to display the obtained image information corresponding to the target point of interest.

In various embodiments, a non-transitory computer-readable medium with instructions stored thereon, that when executed by a processor, perform the processes including: obtaining a detection result (e.g., one or more detection results) of a point of interest (e.g., first point of interest) in an image (e.g., a medical image, such as an original image), where the detection result includes image information (e.g., first image information) and one or more attribute parameters corresponding to the point of interest; obtaining one or more attribute parameter thresholds entered by a user (e.g., in real time); obtaining image information (e.g., second image information) of a target point of interest (e.g., second point of interest) from the image information of the point of interest based on at least comparing the one or more attribute parameters with the one or more attribute parameter thresholds; and displaying the obtained image information corresponding to the target point of interest.

In some examples, the obtained detection result of the point of interest, the included image information and attribute parameter(s) of the point of interest, and their relationship to the attribute parameter threshold(s) input or entered by a user (e.g., obtained in real time) can be used to obtain a comparison result, which can be used to obtain image information of a target point of interest from the detection result of the point of interest, the obtained image information can then displayed while enabling the user to perform adjustment of attribute parameter thresholds in real time, to provide real-time display of detection result under different attribute parameter thresholds beneficial to the user in achieving different degrees of balance between diagnostic accuracy and reading time according to different usage scenarios and different case characteristics, which improves the versatility of computer-aided diagnosis systems.

FIG. 1 is a simplified diagram showing a method S100 for displaying a point of interest of an image, according to some embodiments of the present invention. This diagram is merely an example, which should not unduly limit the scope of the claims. One of ordinary skill in the art would recognize many variations, alternatives, and modifications. The method S100 includes a process S101 of obtaining a detection result of a point of interest in an original image, where the detection result includes image information and one or more attribute parameters corresponding to the point of interest, a process S103 of obtaining one or more attribute parameter thresholds entered by a user in real time, a process S105 of obtaining image information of a target point of interest from the image information of the point of interest based on at least comparing the one or more attribute parameters with the one or more attribute parameter thresholds, and a process S107 of displaying the obtained image information corresponding to the target point of interest. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced. In some examples, the method S100 can be performed by a displaying system (e.g., displaying system 600 or displaying system 900) and/or by a computer-aided diagnosis system of a terminal (e.g., terminal 1000). The terminal can be a hardware device with an operating system, such as a mobile phone, a tablet computer, a palmtop computer, or a personal digital assistant.

In some embodiments, the original image (which may simply be referred to as the image) obtained in process S101 includes a projection image obtained by an imaging system, such as a single module imaging system, such as a computed tomography (CT) system, an emission computed tomography (ECT), an ultrasound imaging system, an X-ray optical imaging system, a positron emission tomography (PET) system, or the like. In certain examples, the imaging system is a multimode imaging system, such as a computed tomography-magnetic resonance imaging (CT-MRI) system, a positron emission tomography-magnetic resonance imaging (PET-MM) system, a single photon emission tomography-computed tomography (SPECT-CT) system, a digital subtraction angiography-computed tomography (DSA-CT) system, or the like. In some examples, the image includes a reconstructed image obtained by reconstructing a projected image.

In certain embodiments, the detection result of the point of interest (e.g., in the original image) is an output result obtained by processing the corresponding image (e.g., partial image selected from the original image) by a deep learning model. In various examples, the detection result includes image information (which may be simply referred to as information) of the point of interest and one or more attribute parameters of the point of interest. In certain examples, the point of interest (which can include multiple points of interest) includes an anatomical structure, such as a blood vessel, an ossification center, a nerve, a muscle, a soft tissue, a trachea, a cartilage, a ligament, and/or a fracture. In some examples, the point of interest includes a lesion, such as a tissue and/or an organ affected by pathogenic factors. In various examples, the point of interest includes a part of the body where the lesion occurs, such as a fracture, a lung nodule, a tumor, a cerebral hemorrhage, a heart disease, a neurological disease, and/or the like. In certain examples, the point of interest includes a body part including a feature.

In some embodiments, an attribute parameter is a parameter affective to the detection result of the point of interest and can be adjusted (e.g., in real time) during use of a displaying device. In certain examples, the one or more attribute parameters included in the detection result includes a confidence level, a category, and a size of the point of interest. In some examples, the confidence level is the degree of confidence that a region or part of the image detected by a detection model, such as a trained deep learning model. In various examples, the size is a parameter for characterizing the size of the region or part of the image to which the point of interest corresponds. In certain examples, the point of interest includes points of interest and the image information corresponds to all points of interest or part of the points of interest.

In various embodiments, the one or more attribute parameter thresholds obtained at the process S103 corresponds to the one or more attribute parameters included in the detection result of the point of interest. In certain examples, the one or more attribute parameter thresholds corresponds to the confidence level, the category, and/or the size of the point of interest. In some examples, a user can adjust the one or more attribute parameter thresholds as needed, such as in real time. In some embodiments, the process S103 is implemented by adopting method S200.

Figure 2:
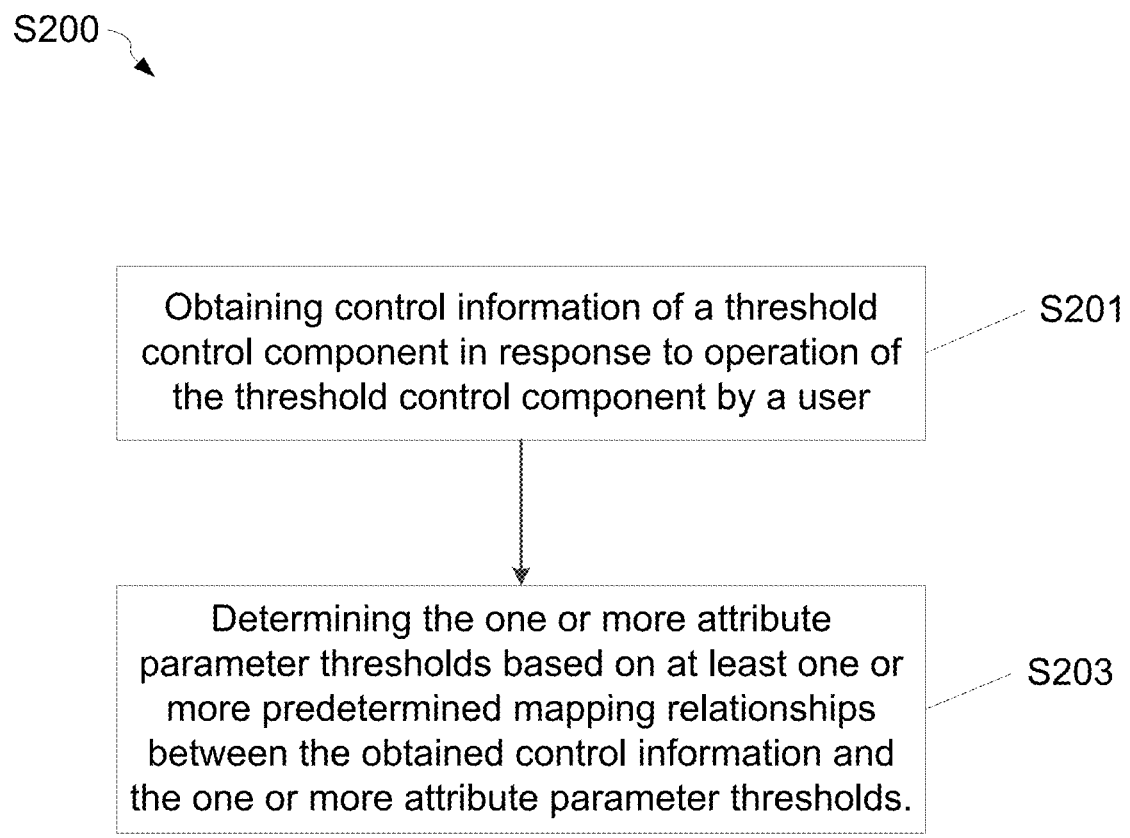
FIG. 2 is a simplified diagram showing a method for obtaining an attribute parameter threshold, according to some embodiments of the present invention.

FIG. 2 is a simplified diagram showing a method S200 for obtaining an attribute parameter threshold, according to some embodiments of the present invention. This diagram is merely an example, which should not unduly limit the scope of the claims. One of ordinary skill in the art would recognize many variations, alternatives, and modifications. The method S200 includes a process S201 of obtaining control information of a threshold control component in response to operation of the threshold control component by a user and a process S203 of determining the one or more attribute parameter thresholds based on at least one or more predetermined mapping relationships between the obtained control information and the one or more attribute parameter thresholds. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In some embodiments, the threshold control component in process S201 is set in a control interface (e.g., an interaction interface), such as a slider (e.g., a slide bar), a pull-down menu, and the like. When the user operates on the threshold control component, an operation information of the threshold control component is obtained in response to the operation. For example, when the user operates the slider, a position information of the slider is obtained.

In some embodiments, the one or more predetermined mapping relationships between the obtained control information and the one or more attribute parameter thresholds in process S203 is determined in advance. For example, the one or more mapping relationships between the control information (e.g., position information) set by the threshold control component (e.g., a slider) and the one or more attribute parameter thresholds may be predetermined.

In certain examples, the relationship between the control information set by the threshold control component and the one or more attribute parameter thresholds may be a linear mapping relationship or a nonlinear relationship. In various examples, when the control information set by the threshold control component is obtained, the corresponding mapping relationship transform the control information to the one or more attribute parameter thresholds. In some examples, the transforming step is based on looking up a mapping relationship table.

Referring to the process S105, in some embodiments, when the attribute parameter of the point interest is confidence level, the process S105 includes determining whether the confidence level of the point of interest is greater or equal to a confidence level threshold (e.g., determined by the threshold control component), which is considered as an attribute parameter threshold. In various embodiments, when the determination result is yes (e.g. when the attribute parameter of the point of interest is greater or equal to the attribute parameter threshold), the process S105 includes obtaining image information of a target point of interest from the image information of the point of interest where the corresponding attribute parameter satisfies (e.g., greater or equal to) the attribute parameter threshold. In some embodiments, an attribute parameter can satisfy a corresponding attribute parameter threshold by being greater, equal to, or less than the attribute parameter threshold. In certain examples, when the attribute parameter of the point interest is size, the process S105 includes determining whether the size of the point of interest is greater or equal to a size threshold (e.g., determined by the threshold control component), which is considered as an attribute parameter threshold. In some examples, when the attribute parameter of the point interest is category, the process S105 includes determining whether the category of the point of interest is equal to the category target (e.g., determined by the threshold control component), which is considered as an attribute parameter threshold.

In some embodiments, the target point of interest includes multiple target points of interest, in which the amount of the multiple target points of interest may be determined by the one or more attribute parameter thresholds. Regarding the process S107, in certain embodiments, when displaying the image information associated with the target point of interest, one or more partial images of the one or more target points of interest are displayed. In certain examples, the process S107 of displaying the image information corresponding to the target point of interest includes a process S109 of obtaining one or more partial images corresponding to one or more target points of interest, a process S111 of rendering the one or more partial images, and a process S113 of displaying the rendered one or more partial images. In some examples, rendering a partial image includes using Multi-Planner Reformation (MPR), Volume Rendering Technique (VRT), Maximum Intensity Projection (MIP), and/or Curved Planar Reformat (CPR).

In certain embodiments, MPR is used to superimpose axial images in a scanning range to reconstruct the coronal, sagittal, and arbitrary angular oblique images of a tissue specified by recombination lines marked by some of the reticle. In some examples, MPR can be used to generate new tomographic images without repeated scanning, and the surface recombination can be expanded in an image to show the growth of curved objects.

In certain embodiments, VRT is used to make an assumed projection line pass through a scan volume from a given angle, and comprehensively display pixel information in the volume. In some examples, VRT gives an image different pseudo-color and transparency, giving a sense of approximate sturdy three-dimensional structure, with little data information lost in the reconstruction, and can display the anatomical structure or spatial relationship of the lesion well.

In certain embodiments, MIP is a computer visualization method used for projecting three-dimensional spatial data onto a visualization plane. In some examples, along the parallel rays from the viewpoint to the projection plane, the brightness of each voxel density value is attenuated, and finally the voxel with the highest brightness is presented on the projection plane. In certain examples, MIP is performed on already imaged image to display the perspective effect of the region corresponding to the point of interest. In various examples, when the projection plane is rotated by an angle for each step, MIP is performed after each rotational step, MIPs from the various steps are stacked to obtain a rotatable region corresponding to the point of interest.

In certain embodiments, CPR is a special method of MPR used for displaying an organ with curved structure, such as a jaw bone, a tortuous blood vessel, a bronchus, etc.

In some embodiments, the image information of the target point of interest may include location information of the target point of interest and/or size information of the target point of interest. In various embodiments, the process S107 of displaying the image information corresponding to the target point of interest includes a process S115 of obtaining an original image, a process S117 of determining a target region of interest corresponding to the target point of interest in the original image based on at least location information and size information of the target point of interest, and a process S119 of displaying the original image including the target region of interest. In certain examples, the original image is an image of various modalities obtained directly or indirectly by one or more imaging systems.

In some embodiments, the process S107 of displaying information associated with the target point of interest includes a process S121 of generating a target index corresponding to the image information of the target point of interest and a process S123 of displaying the target index. In certain examples, the target index includes a serial number, such as a number in the form of an Arabic numeral, and a part of a shortened target interest information, such as a general location of the target point of interest. In various examples, displaying the target index includes displaying a serial number, such as in a sorted order.

Figure 3:
FIG. 3 is a representative view showing an interface for displaying information of a target of interest, according to some embodiments of the present invention.
Figure 4:
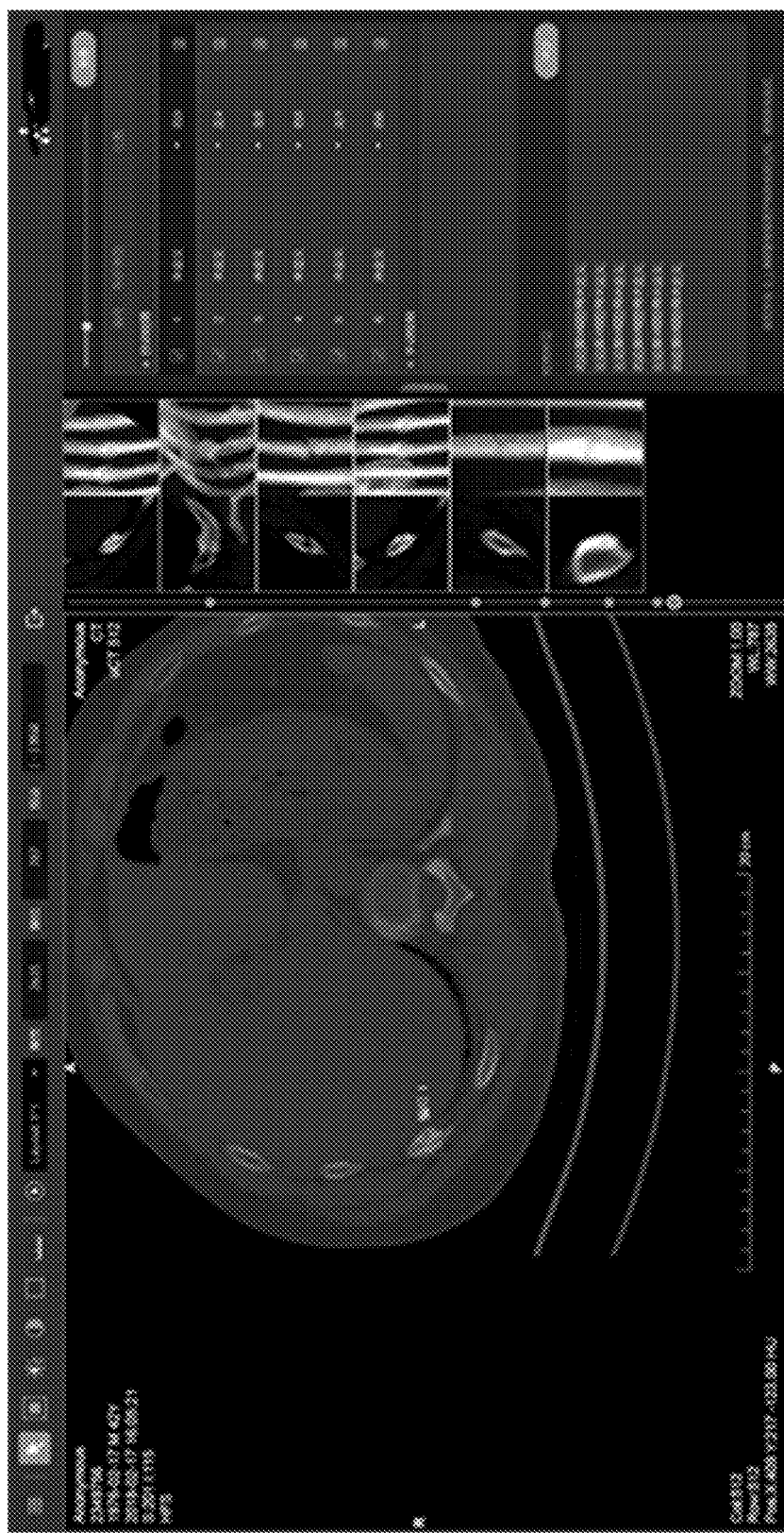
FIG. 4 is a representative view showing another interface for displaying information of a target of interest, according to some embodiments of the present invention.

FIG. 3 and FIG. 4 are representative views showing an interface for displaying information of a target of interest (e.g., with different confidence level thresholds selected), according to some embodiments of the present invention. As shown in FIG. 3 and FIG. 4, a threshold control component is disposed on the interface (e.g., a human-computer interaction interface) in the form of a slider on a sliding bar. In some examples, the slider position of the slider corresponds to a threshold value of an attribute parameter threshold. In certain examples, the closer the slider position is to a first side (e.g., the right side) of the slider bar, the greater the attribute parameter threshold (e.g., confidence threshold), which can be determined based on at least the mapping relationship between the slider position and the attribute parameter threshold. In some examples, the closer the slider position is to a second side (e.g., the left side) of the slider bar opposite of the first side, the lesser the attribute parameter threshold (e.g., confidence threshold), which can be determined based on at least the mapping relationship between the slider position and the attribute parameter threshold. For example, the leftmost end of the slider bar is set to correspond to a preset minimum threshold (e.g., 0), and the rightmost end of the slider bar corresponds to a preset maximum threshold (e.g., 1.0). In the illustrative examples of FIG. 3 and FIG. 4, the attribute parameter threshold (e.g., confidence threshold) corresponding to the slider position of the slider is large in FIG. 3, and the attribute parameter threshold (e.g., confidence threshold) corresponding to the slider position of the slider is small in FIG. 4. As shown, FIG. 3 and FIG. 4, while showing the same original image, when under different confidence thresholds, different amount of target points of interest are obtained. In certain examples, the amount of target points of interest is included in the serial number of a target index. In some examples, the target index includes information of the general location of the target point of interest.

Figure 5:
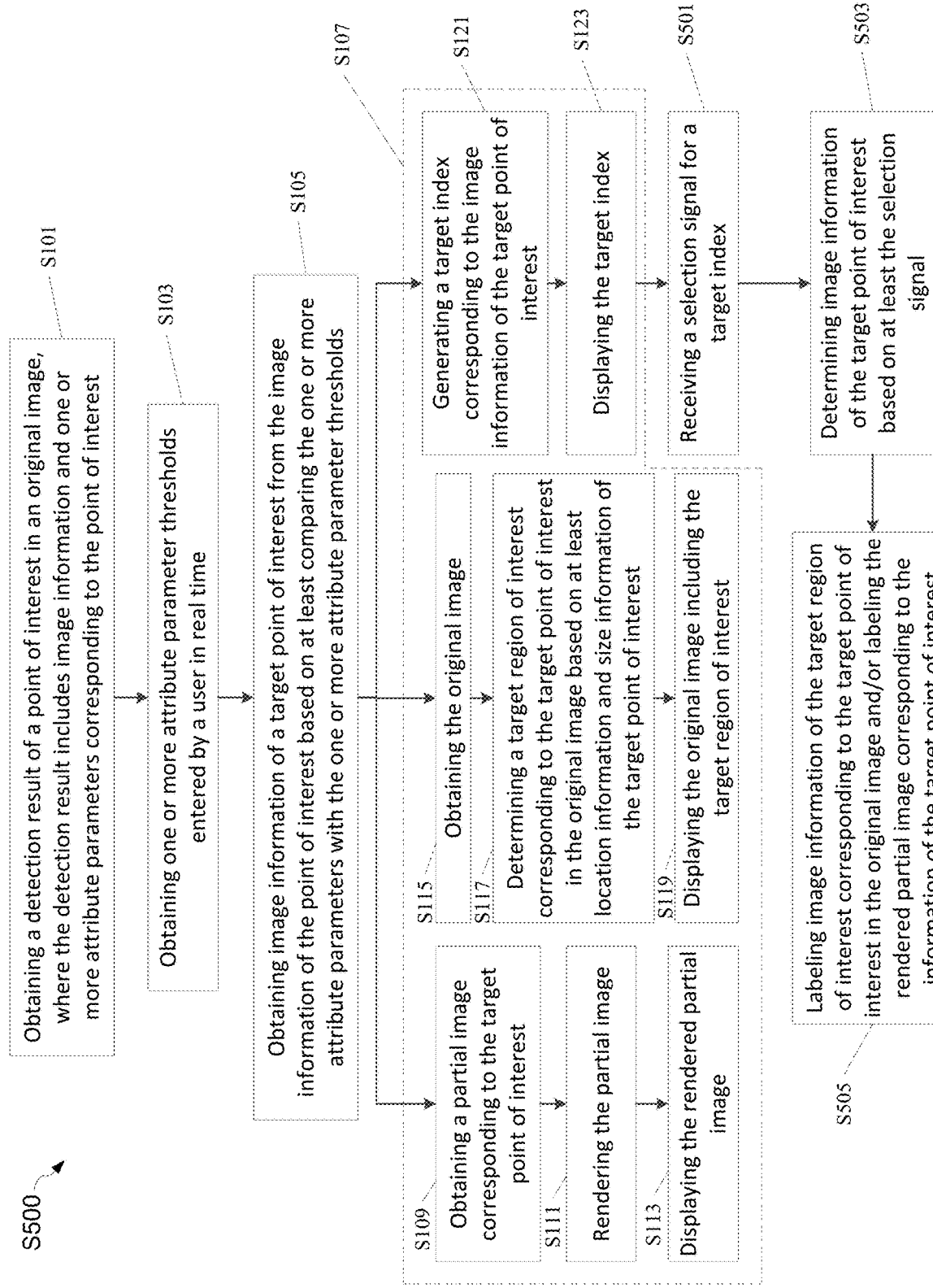
FIG. 5 is a simplified diagram showing another method for displaying a point of interest of an image, according to some embodiments of the present invention.

FIG. 5 is a simplified diagram showing another method S500 for displaying a point of interest of an image, according to some embodiments of the present invention. This diagram is merely an example, which should not unduly limit the scope of the claims. One of ordinary skill in the art would recognize many variations, alternatives, and modifications. The method S500 is substantially similar to the method S100, specifically, including the processes of S101, S103, S105, and S107 and additionally a process S501 of receiving a selection signal for a target index, a process S503 of determining image information of the target point of interest based on at least the selection signal, and a process S505 of labeling image information of the target region of interest corresponding to the target point of interest in the original image and/or labeling the rendered partial image corresponding to the information of the target point of interest. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In various embodiments, the process S501 of receiving a selection signal for a target index includes receiving a selection signal selected by a user using an interface (e.g., human-machine interface).

In some embodiments, in the process S503 includes determining information of the target point of interest corresponding to a selected target index indicated by the selection signal, since the information corresponding to the target region of interest has been determined, following determining the point of interest based on the received selection signal, the information associated with the target point of interest is next determined and labeled. As an example, as shown in FIG. 3 and FIG. 4, the information corresponding to the target point of interest identified in the displayed original image is shown on the left of the display window, with a target index selection window on the right side of the interface. In certain examples, each target index corresponds to a target region of interest and/or a target point of interest. In some examples, the process S505 includes rendering a partial image corresponding to the information of the target point of interest and/or the target region of interest.

In various embodiments, a user can adjust an attribute parameter threshold in real time, such that detection result under different attribute parameter thresholds can be displayed in real time, which can be beneficial to the user for weighing different usage scenarios and different case characteristics to achieve different degrees of balance between diagnostic accuracy and reading time to improve the versatility of computer-aided diagnostic systems.

Figure 6:
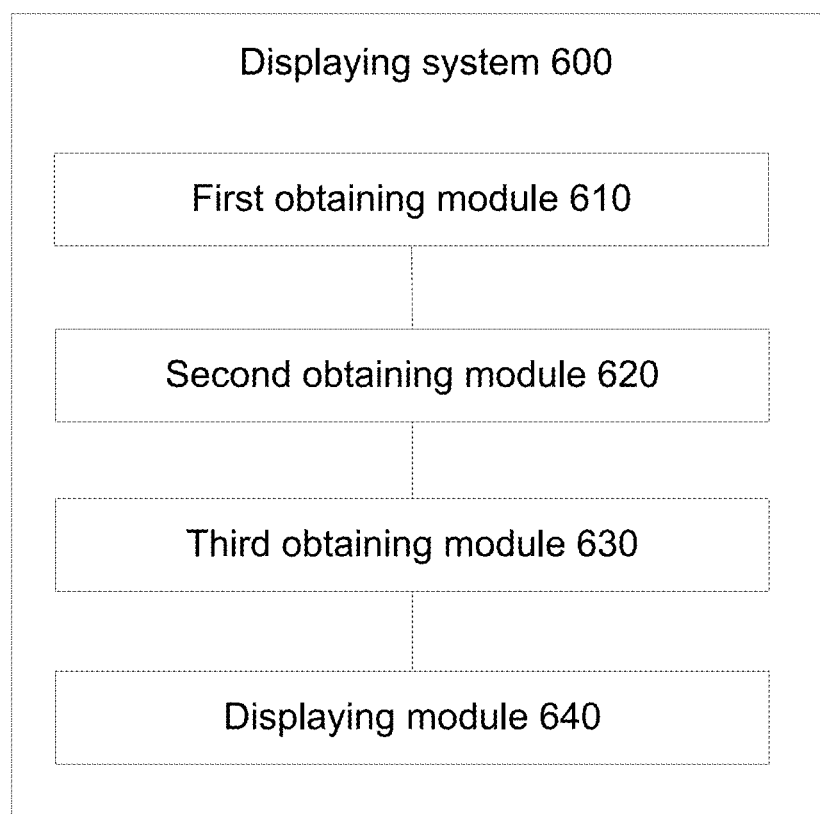
FIG. 6 is a simplified diagram showing a displaying system for displaying a point of interest of an image, according to some embodiments.

FIG. 6 is a simplified diagram showing a displaying system 600 for displaying a point of interest of an image, according to some embodiments. This diagram is merely an example, which should not unduly limit the scope of the claims. One of ordinary skill in the art would recognize many variations, alternatives, and modifications. In some examples, the displaying system 600 is configured to perform the method S100, the method S201, and/or the method S500, either entirely or partially. In some examples, the displaying system 600 includes a first obtaining module 610, a second obtaining module 620, a third obtaining module 630, and a displaying module 640. Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In some embodiments, the first obtaining module 610 is configured to obtain a detection result of a point of interest (e.g., one or more points of interest) in an image (e.g., original image), where the detection result of the point of interest includes information of the point of interest and one or more attribute parameters of the point of interest.

In some embodiments, the second obtaining module 620 is configured to obtain one or more attribute parameter thresholds, such as one or more attribute parameter thresholds input or entered by a user, such as in real time. In some embodiments, the third obtaining module 630 is configured to obtain information corresponding to a target point of interest from the detection result of the point of interest. In some embodiments, the displaying module 640 is configured to display information corresponding to the target point of interest. In certain examples, the one or more attribute parameters corresponding to the point of interest includes confidence level, category, and/or size. In certain examples, the point of interest includes an anatomical structure or a lesion.

Figure 7:
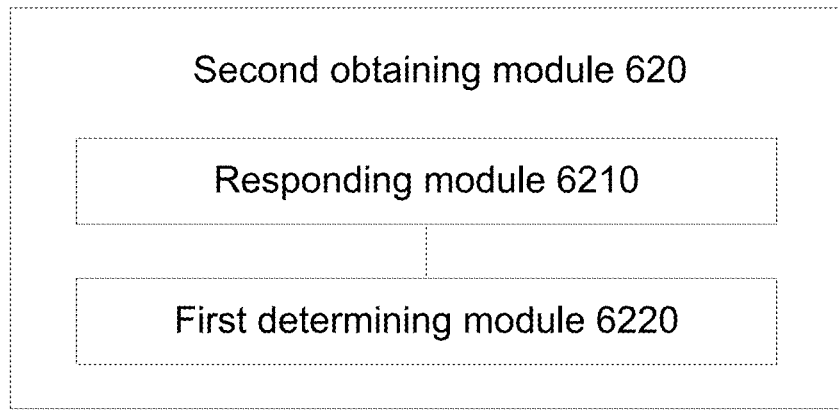
FIG. 7 is a simplified diagram showing a second obtaining module, according to some embodiments.

FIG. 7 is a simplified diagram showing a second obtaining module 620, according to some embodiments. This diagram is merely an example, which should not unduly limit the scope of the claims. One of ordinary skill in the art would recognize many variations, alternatives, and modifications. In some examples, the second obtaining module 6210 includes a responding module 6210 and a first determining module 6220. Although the above has been shown using a selected group of components for the module, there can be many alternatives, modifications, and variations. For example, some of the components may be expanded and/or combined. Other components may be inserted to those noted above. Depending upon the embodiment, the arrangement of components may be interchanged with others replaced.

In some embodiments, the responding module 6210 is configured to obtain control information corresponding to the threshold control component in response to operation of the threshold control component by a user. In some embodiments, the first determining module 6220 is configured to determine an attribute parameter threshold value entered by the user, such as based on at least a mapping relationship (e.g., predetermined) between the control information (e.g., selected using the threshold control component) and the attribute parameter threshold.

Figure 8:
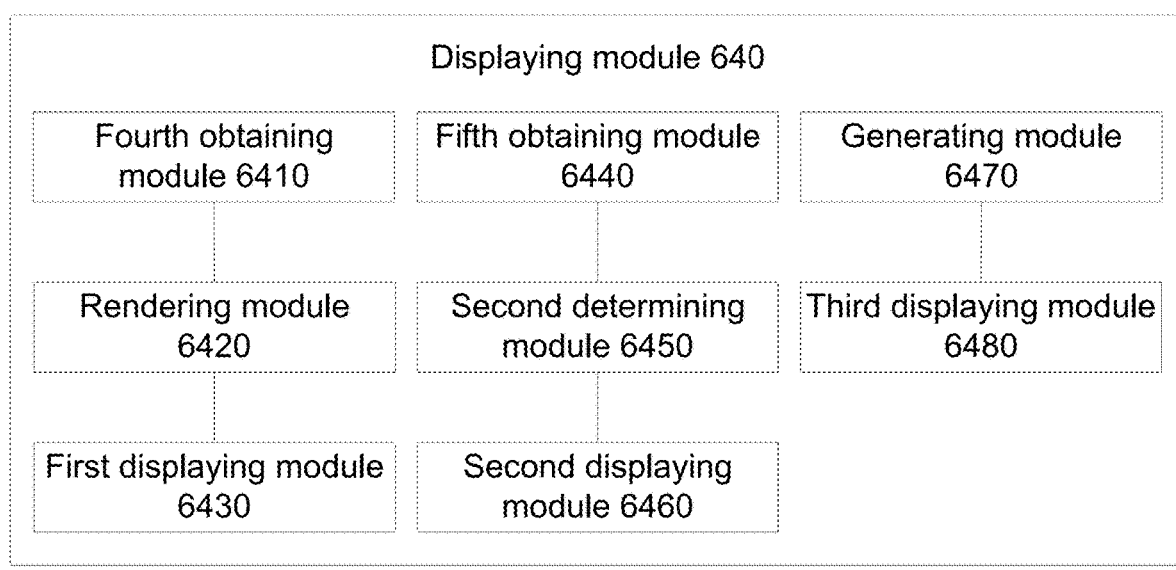
FIG. 8 is a simplified diagram showing a displaying module, according to some embodiments.

FIG. 8 is a simplified diagram showing a displaying module 640, according to some embodiments. This diagram is merely an example, which should not unduly limit the scope of the claims. One of ordinary skill in the art would recognize many variations, alternatives, and modifications. In some examples, the displaying module 640 includes a fourth obtaining module 6410, a rendering module 6420, a first displaying module 6430. Although the above has been shown using a selected group of components for the module, there can be many alternatives, modifications, and variations. For example, some of the components may be expanded and/or combined. Other components may be inserted to those noted above. Depending upon the embodiment, the arrangement of components may be interchanged with others replaced.

In various embodiments, the fourth obtaining module 6410 is configured to obtain a partial image corresponding to a target point of interest. In certain embodiments, the rendering module 6420 is configured to render the partial image. In some embodiments, the first display module 6430 is configured to display the rendered partial image.

In various examples, the information of the target point of interest includes the location information of the target point of interest and the size information of the target point of interest. In certain examples, the fifth obtaining module 6440 is configured to obtain an original image. In some examples, the second determining module 6450 is configured to determine a target region of interest corresponding to the target point of interest in the original image, such as based on at least the location information of the target point of interest and/or the size information of the target point of interest. In certain examples, the second display module 6460 is configured to display the original image including (or showing) the target region of interest.

In certain embodiments, the generating module 6470 is configured to generate a target index corresponding to the information of the target point of interest. In some examples, the third displaying module 6480 is configured to display the target index.

Figure 9:
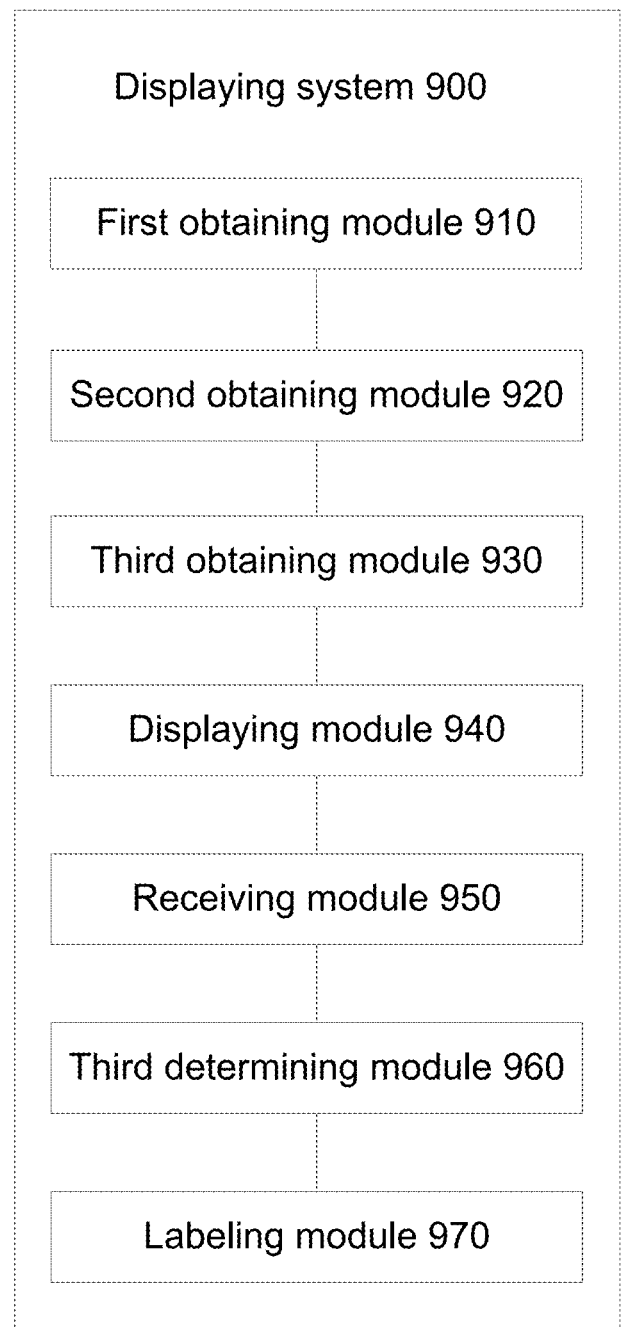
FIG. 9 is a simplified diagram showing another displaying system for displaying a point of interest of an image, according to some embodiments.

FIG. 9 is a simplified diagram showing another displaying system 900 for displaying a point of interest of an image, according to some embodiments. This diagram is merely an example, which should not unduly limit the scope of the claims. One of ordinary skill in the art would recognize many variations, alternatives, and modifications. In some examples, the displaying system 900 includes a first obtaining module 910, a second obtaining module 920, a third obtaining module 930, a displaying module 940, a receiving module 950, a third determining module 960, and a labeling module 970. Although the above has been shown using a selected group of components for the system, there can be many alternatives, modifications, and variations. For example, some of the components may be expanded and/or combined. Other components may be inserted to those noted above. Depending upon the embodiment, the arrangement of components may be interchanged with others replaced.

In various embodiments, the first obtaining module 910 is substantially similar or identical to the first obtaining module 610, the second obtaining module 920 is substantially similar or identical to the second obtaining module 620, the third obtaining module 930 is substantially similar or identical to the third obtaining module 630, and/or the displaying module 940 is substantially similar or identical to the displaying module 640.

In some embodiments, the receiving module 950 is configured to receive a selection signal for a target index, such as a target index selected from multiple target indices. In certain embodiments, the third determining module 960 is configured to determine information corresponding to a target point of interest based on at least the target index selected by the selection signal. In various examples, the labeling module 970 (which may be referred to as the marking module or the tagging module) is configured to label a target region of interest corresponding to the information of the target point of interest, and/or a rendered partial image corresponding to the information of the target point of interest.

In certain embodiments, the displaying system and/or method for displaying a point of interest of an image enables a user to adjust a threshold of an attribute parameter in real time, so that the detection result under different attribute parameter thresholds can be displayed in real time, which is beneficial to the user according to different usage scenarios and different case characteristics to achieve the balance between diagnostic accuracy and read time, thus increasing the versatility of computer-aided diagnostic systems.

Figure 10:
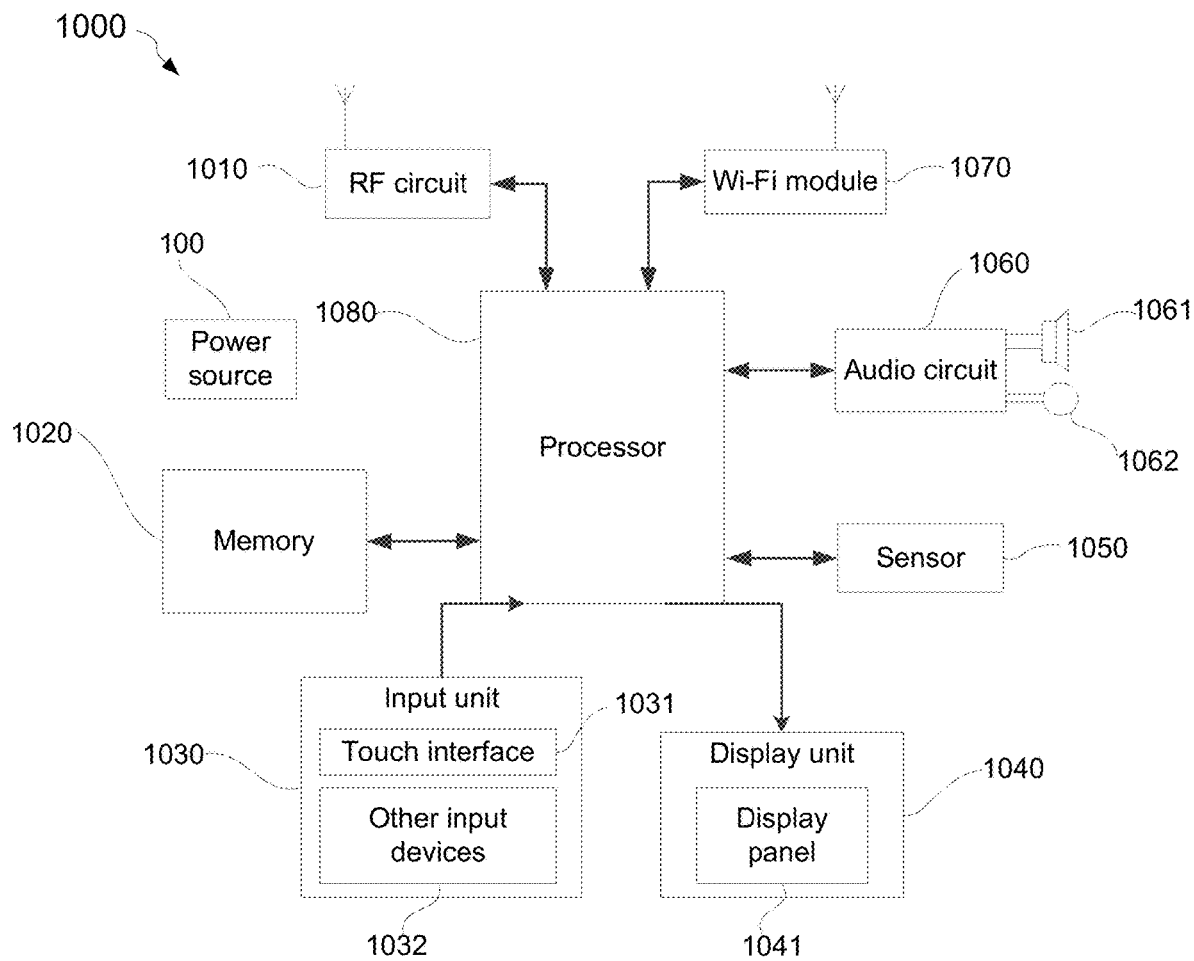
FIG. 10 is a simplified diagram showing a terminal, according to some embodiments.

FIG. 10 is a simplified diagram showing a terminal 1000, according to some embodiments. This diagram is merely an example, which should not unduly limit the scope of the claims. One of ordinary skill in the art would recognize many variations, alternatives, and modifications. In some examples, the terminal 1000 includes a RF (Radio Frequency) circuit 1010, a memory 1020 including one or more computer-readable (e.g., processor-executable) storage media, an input unit 1030, a display unit 1040, a sensor (e.g., video sensor) 1050, an audio circuit 1060, and a Wi-Fi (Wireless Fidelity) module 1070, a processor including one or more processing cores, and a power supply 100. In various examples, the terminal 1000 is configured to perform the method S100, the method S200, and/or the method S500. Although the above has been shown using a selected group of components for the terminal, there can be many alternatives, modifications, and variations. For example, some of the components may be expanded and/or combined. Other components may be inserted to those noted above. Depending upon the embodiment, the arrangement of components may be interchanged with others replaced. In some examples, the terminal is a computer.

In various embodiments, the RF circuit 1010 is configured for receiving and transmitting signals during and after receiving or transmitting information, for example, receiving downlink information of the base station and then processing it by the processor 1080, and/or transmitting uplink data to a base station. In some examples, the RF circuit 1010 includes, an antenna, an amplifier, a tuner, an oscillator, a Subscriber Identity Module (SIM) card, a transceiver, a coupler, an LNA (Low Noise Amplifier), and/or a duplexer. In certain examples, they RF circuit 1010 is configured to communicate with the network and other devices via wireless communication, such as by using a communication standard or protocol such as GSM (Global System of Mobile communication), GPRS (General Packet Radio Service), CDMA (Code Division Multiple Access), WCDMA (Wideband Code Division Multiple Access), LTE (Long Term Evolution), e-mail, and/or SMS (Short Messaging Service).

In various embodiments, the memory 1020 is configured to store software programs and modules and the processor 1080 is configured to execute various functional applications and data processing by running software programs and modules stored in the memory 1020. In certain embodiments, the memory 1020 includes a storage program region and a storage data region, wherein the storage program region is configured to store an operating system, an application required for at least one function (e.g., a sound-playing function, an image-playing function, etc.), and the storage data region configured to store data created by the use of the terminal 1000 (e.g., video data, phone book, etc.). In some examples, the memory 1020 includes high speed random access memory and/or non-volatile memory, such as a magnetic disk storage device, a flash memory device, or another volatile solid-state storage device. In various examples, memory 1020 includes a memory controller for providing access to the memory 1020 from the processor 1080 and/or the input unit 1030.

In certain embodiments, the input unit 1030 is configured to receive input numeric or character information, as well as signal inputs related to user settings and function controls inputted or generated via keyboard, mouse, joystick, optical or trackball devices. In various examples, the input unit 1030 includes an image input device 1031 and other input devices 1032. In some embodiments, the image input device 1031 includes a camera and/or an optical scanning device. In certain embodiments, the other input devices 1032 include one or more of a physical keyboard, function keys (e.g., volume control buttons, switch buttons, etc.), trackballs, mice, joysticks, and the like.

In some embodiments, the display unit 1040 is configured to display information entered by a user such as via various graphical user interfaces of terminal 1000. As an example, the interface includes graphics, text, icons, video, and any combination thereof. In certain examples, the display unit 1040 includes a display panel 1041, which in various examples, includes a LCD (Liquid Crystal Display), an OLED (Organic Light-Emitting Diode), or the like.

In various embodiments, the terminal 1000 includes at least one video sensor 1050 for acquiring video information of a user. Terminal 1000 may also include other sensors (not shown) such as light sensors, motion sensors, and other sensors. Specifically, the light sensor may include an ambient light sensor and/or a proximity sensor, wherein the ambient light sensor may adjust the brightness of the display panel 1041 according to the brightness of the ambient light, and the proximity sensor may turn off the display panel 1041 when the terminal 1000 moves close to the ear or backlight. When a motion sensor is used, the gravity acceleration sensor can detect the magnitude of acceleration in all directions (e.g., three axes). When stationary, the motion sensor is configured to detect the magnitude and direction of gravity. The sensor can be used to identify gestures applied to or near a mobile device (e.g., horizontal and vertical screen switching, related game-controls, magnetometer attitude calibration), and/or vibration recognition related functions (such as pedometer, tapping). In some embodiments, the terminal 1000 includes a gyroscope, a barometer, a hygrometer, a thermometer, an infrared sensor, and/or a sensor of other types.

In various examples, the video circuit 1060, speaker 1061, and microphone 1062 are configured to provide a video interface between the user and terminal 1000. The audio circuit 1060 can transmit converted electrical data of the received audio data to the speaker 1061, which is then converted it into a sound signal output using the speaker 1061. In certain examples, the microphone 1062 is configured to convert the collected sound signal into an electrical signal, and after receiving the electrical signal using the audio circuit 1060, the electrical signal is converted into audio data, which is next processed by the audio data output processor 1080, which is for example, then sent to another terminal via the RF circuit 1011, or outputted to the memory 1020 for further processing. The audio circuit 1060 may also include a headphone jack to provide communication of the peripheral earphones with the terminal 1000.

In various embodiments, Wi-Fi is used as a short-range wireless transmission technology to send and receive emails, browse web pages, and access streaming media through the Wi-Fi module 1070, which provides users with wireless broadband Internet access.

In some examples, the processor 1080 is configured to function as the control center of the terminal 1000 for connecting various portions of the terminal (e.g., a mobile device) using various interfaces and connection lines, running or executing software programs and/or modules stored in memory 1020, and recalling data stored in memory 1020. In various examples, the functions and processing data of the terminal 1000 are executed to perform overall monitoring of the terminal. In certain examples, the processor 1080 includes one or more processing cores, and/or is configured to integrate an application processor and a modem processor, where the application processor is configured to process or run an operating system, a user interface, or an application. A modem processor, when included, can be configured to handle wireless communications.

In various embodiments, the terminal 1000 includes a power source 100 (such as a battery) for supplying power to various components of the terminal 1000. In some examples, the power source 100 is logically coupled to the processor 1080 through a power management system to manage functions such as charging, discharging, and power management through the power management system. In certain examples, the power supply 100 includes any one or more of a DC or AC power source, a recharging system, a power failure detection circuit, a power converter or inverter, a power status indicator, and the like. In some examples, the terminal 1000 includes a Bluetooth module or the like.

In certain embodiments, the terminal 1000 includes a memory storing one or more programs, which when executed a processor, perform processes associated with the display method S100 and/or method S500.

In various embodiments, a computer-implemented method for displaying one or more regions of interest of an original image includes obtaining one or more detection results of one or more first regions of interest. In some examples, each detection result of the one or more detection results corresponding to one first region of interest of the one or more first regions of interest. In certain examples, each detection result including image information and one or more attribute parameters for their corresponding first region of interest. In various examples, the method further includes obtaining one or more attribute parameter thresholds provided by a user in real time. In some examples, each attribute parameter threshold of the one or more attribute parameter thresholds corresponding to one attribute parameter of the one or more attribute parameters. In various examples, the method includes obtaining one or more second regions of interest from the one or more first regions of interest based on at least comparing the one or more attribute parameters with the one or more attribute parameter thresholds respectively. In various examples, the method includes displaying image information corresponding to each second region of interest of the one or more second regions of interest. In some examples, the method is implemented according to at least the method S100 of FIG. 1. In certain examples, the method is implemented by at least the displaying system 600 of FIG. 6 and/or the displaying system 900 of FIG. 9.

In some embodiments, the one or more attribute parameters include at least one selected from a group consisting of confidence level, category, and size.

In some embodiments, the obtaining one or more attribute parameter thresholds input by a user in real time includes obtaining one or more control information of a threshold control component in response to operation of the threshold control component by the user and determining the one or more attribute parameter thresholds based on at least one or more predetermined mapping relationships between the one or more control information and the one or more attribute parameter thresholds.

In some embodiments, the displaying image information corresponding to each second region of interest of the one or more second regions of interest includes obtaining one or more partial images from the original image, each of the one or more partial images corresponding to one second region of interest of the one or more second regions, rendering the one or more partial images, and displaying the rendered one or more partial images.

In some embodiments, the image information corresponding to each second region of interest of the one or more second regions of interest includes at least one selected from a group consisting of location and size and wherein displaying image information corresponding to each second region of interest of the one or more second regions of interest includes obtaining the original image, obtaining the one or more second regions of interest from the original image based on at least the image information corresponding to each second region of interest, and displaying one or more partial images from the original image, each of the one or more partial images corresponding to one second region of interest of the one or more second regions.

In some embodiments, displaying image information corresponding to each second region of interest of the one or more second regions of interest includes generating one or more target indices corresponding to image information corresponding to the one or more second regions of interest respectively and displaying the one or more target indices.

In some embodiments, the computer-implemented method further includes receiving a selection signal for one target index of the one or more target indices; selecting one second region of interest of the one or more second regions of interest based on at least its corresponding image information corresponding to the selected one target index; and labeling at least one of: one of the one or more partial images from the original image corresponding to the selected one target index; and one of the rendered one or more partial images corresponding to the selected one target index.

In some embodiments, the one or more first regions of interest includes an anatomical structure or a lesion.

In various embodiments, a device for displaying a point of interest of an original image includes: a first module configured to obtain one or more detection results of one or more first regions of interest, each detection result of the one or more detection results corresponding to one first region of interest of the one or more first regions of interest, each detection result including image information and one or more attribute parameters for their corresponding first region of interest; a second module configured to obtain one or more attribute parameter thresholds provided by a user in real time, each attribute parameter threshold of the one or more attribute parameter thresholds corresponding to one attribute parameter of the one or more attribute parameters; a third module configured to obtain one or more second regions of interest from the one or more first regions of interest based on at least comparing the one or more attribute parameters with the one or more attribute parameter thresholds respectively; and a displaying module configured to display image information corresponding to each second region of interest of the one or more second regions of interest. In some examples, the device is implemented according to at least the displaying system 600 of FIG. 6 and/or the displaying system 900 of FIG. 9.

In some embodiments, the one or more attribute parameters include at least one selected from a group consisting of confidence level, category, and size.

In some embodiments, the second module is configured to: obtain one or more control information of a threshold control component in response to operation of the threshold control component by the user; and determine the one or more attribute parameter thresholds based on at least one or more predetermined mapping relationships between the one or more control information and the one or more attribute parameter thresholds.

In some embodiments, the displaying module is configured to: obtain one or more partial images from the original image, each of the one or more partial images corresponding to one second region of interest of the one or more second regions; render the one or more partial images; and display the rendered one or more partial images.

In some embodiments, the second information corresponds to the one or more target points of interest includes at least one of location and size, and the displaying module is configured to: obtain the original image; obtain the one or more second regions of interest from the original image based on at least the image information corresponding to each second region of interest; and display one or more partial images from the original image, each of the one or more partial images corresponding to one second region of interest of the one or more second regions.

In some embodiments, the displaying module is configured to: generate one or more target indices corresponding to image information corresponding to the one or more second regions of interest respectively; and display the one or more target indices.

In various embodiments, a non-transitory computer-readable medium with instructions stored thereon, that when executed by a processor, perform the processes including: obtaining one or more detection results of one or more first regions of interest, each detection result of the one or more detection results corresponding to one first region of interest of the one or more first regions of interest, each detection result including image information and one or more attribute parameters for their corresponding first region of interest; obtaining one or more attribute parameter thresholds provided by a user in real time, each attribute parameter threshold of the one or more attribute parameter thresholds corresponding to one attribute parameter of the one or more attribute parameters; obtaining one or more second regions of interest from the one or more first regions of interest based on at least comparing the one or more attribute parameters with the one or more attribute parameter thresholds respectively; and displaying image information corresponding to each second region of interest of the one or more second regions of interest. In some examples, the non-transitory computer-readable medium with instructions stored thereon is implemented according to at least the method S100 of FIG. 1 and/or the terminal 1000 of FIG. 10.

In some embodiments, the one or more attribute parameters include at least one selected from a group consisting of confidence level, category, and size.

In some embodiments, the non-transitory computer-readable medium, when executed by the processor, perform the processes including: obtaining one or more control information of a threshold control component in response to operation of the threshold control component by the user; and determining the one or more attribute parameter thresholds based on at least one or more predetermined mapping relationships between the one or more control information and the one or more attribute parameter thresholds.

In some embodiments, the non-transitory computer-readable medium, when executed by the processor, perform the processes including: obtaining one or more partial images from the original image, each of the one or more partial images corresponding to one second region of interest of the one or more second regions; rendering the one or more partial images; and displaying the rendered one or more partial images.

In some embodiments, the non-transitory computer-readable medium, wherein the image information corresponding to each second region of interest of the one or more second regions of interest includes at least one selected from a group consisting of location and size; and wherein when executed by the processor, perform the processes including: obtaining the original image; obtaining the one or more second regions of interest from the original image based on at least the image information corresponding to each second region of interest; and displaying one or more partial images from the original image, each of the one or more partial images corresponding to one second region of interest of the one or more second regions.

In some embodiments, the non-transitory computer-readable medium, when executed by the processor, perform the processes including: generating one or more target indices corresponding to image information corresponding to the one or more second regions of interest respectively; and displaying the one or more target indices.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for displaying one or more regions of interest of an original image, the method comprising:
    obtaining one or more detection results of one or more first regions of interest, each detection result of the one or more detection results corresponding to one first region of interest of the one or more first regions of interest, each detection result including image information and one or more attribute parameters for a corresponding first region of interest;
    obtaining one or more attribute parameter thresholds provided by a user in real time, each attribute parameter threshold of the one or more attribute parameter thresholds corresponding to one attribute parameter of the one or more attribute parameters;
    obtaining one or more second regions of interest from the one or more first regions of interest based on at least comparing the one or more attribute parameters with the one or more attribute parameter thresholds respectively; and
    displaying image information corresponding to each second region of interest of the one or more second regions of interest;
    wherein the obtaining one or more attribute parameter thresholds provided by a user in real time includes:
        obtaining one or more control information of a threshold control component in response to operation of the threshold control component by the user; and
        determining the one or more attribute parameter thresholds based on at least one or more predetermined mapping relationships between the one or more control information and the one or more attribute parameter thresholds.

2. The computer-implemented method of claim 1, wherein the one or more attribute parameters include at least one selected from a group consisting of confidence level, category, and size.

3. The computer-implemented method of claim 1, wherein the displaying image information corresponding to each second region of interest of the one or more second regions of interest includes:
    obtaining one or more partial images from the original image, each of the one or more partial images corresponding to one second region of interest of the one or more second regions;
    rendering the one or more partial images; and
    displaying the rendered one or more partial images.

4. The computer-implemented method of claim 3, wherein:
    the image information corresponding to each second region of interest of the one or more second regions of interest includes at least one selected from a group consisting of location and size; and
    wherein the displaying image information corresponding to each second region of interest of the one or more second regions of interest includes:
        obtaining the original image;
        obtaining the one or more second regions of interest from the original image based on at least the image information corresponding to each second region of interest; and
        displaying the one or more partial images from the original image, each of the one or more partial images corresponding to one second region of interest of the one or more second regions.

5. The computer-implemented method of claim 4, wherein the displaying image information corresponding to each second region of interest of the one or more second regions of interest includes:
    generating one or more target indices corresponding to image information corresponding to the one or more second regions of interest respectively; and
    displaying the one or more target indices.

6. The computer-implemented method of claim 5, further comprising:
    receiving a selection signal for one target index of the one or more target indices;
    selecting one second region of interest of the one or more second regions of interest based on at least its corresponding image information corresponding to the selected one target index; and
    labeling at least one of:
        one of the one or more partial images from the original image corresponding to the selected one target index; and
        one of the rendered one or more partial images corresponding to the selected one target index.

7. The computer-implemented method of claim 1, wherein the one or more first regions of interest includes an anatomical structure or a lesion.

8. A device for displaying a point of interest of an original image, the device comprising:
    a first module configured to obtain one or more detection results of one or more first regions of interest, each detection result of the one or more detection results corresponding to one first region of interest of the one or more first regions of interest, each detection result including image information and one or more attribute parameters for a corresponding first region of interest;
    a second module configured to obtain one or more attribute parameter thresholds provided by a user in real time, each attribute parameter threshold of the one or more attribute parameter thresholds corresponding to one attribute parameter of the one or more attribute parameters;
    a third module configured to obtain one or more second regions of interest from the one or more first regions of interest based on at least comparing the one or more attribute parameters with the one or more attribute parameter thresholds respectively; and
    a displaying module configured to display image information corresponding to each second region of interest of the one or more second regions of interest;
    wherein the second module is configured to:
        obtain one or more control information of a threshold control component in response to operation of the threshold control component by the user; and
        determine the one or more attribute parameter thresholds based on at least one or more predetermined mapping relationships between the one or more control information and the one or more attribute parameter thresholds.

9. The device of claim 8, wherein the one or more attribute parameters include at least one selected from a group consisting of confidence level, category, and size.

10. The device of claim 8, wherein the displaying module is configured to:
obtain one or more partial images from the original image, each of the one or more partial images corresponding to one second region of interest of the one or more second regions;
render the one or more partial images; and
display the rendered one or more partial images.

11. A non-transitory computer-readable medium with instructions stored thereon, that when executed by a processor, perform the processes comprising:
obtaining one or more detection results of one or more first regions of interest, each detection result of the one or more detection results corresponding to one first region of interest of the one or more first regions of interest, each detection result including image information and one or more attribute parameters for a corresponding first region of interest;
obtaining one or more attribute parameter thresholds provided by a user in real time, each attribute parameter threshold of the one or more attribute parameter thresholds corresponding to one attribute parameter of the one or more attribute parameters;
obtaining one or more second regions of interest from the one or more first regions of interest based on at least comparing the one or more attribute parameters with the one or more attribute parameter thresholds respectively; and
displaying image information corresponding to each second region of interest of the one or more second regions of interest;
wherein the obtaining one or more attribute parameter thresholds provided by a user in real time includes:
obtaining one or more control information of a threshold control component in response to operation of the threshold control component by the user; and
determining the one or more attribute parameter thresholds based on at least one or more predetermined mapping relationships between the one or more control information and the one or more attribute parameter thresholds.

12. The non-transitory computer-readable medium of claim 11, wherein the one or more attribute parameters include at least one selected from a group consisting of confidence level, category, and size.

13. The non-transitory computer-readable medium of claim 11, when executed by the processor, perform the processes including:
obtaining one or more partial images from an original image, each of the one or more partial images corresponding to one second region of interest of the one or more second regions;
rendering the one or more partial images; and
displaying the rendered one or more partial images.

14. The non-transitory computer-readable medium of claim 11, wherein the image information corresponding to each second region of interest of the one or more second regions of interest includes at least one selected from a group consisting of location and size; and wherein when executed by the processor, perform the processes including:
obtaining the original image;
obtaining the one or more second regions of interest from the original image based on at least the image information corresponding to each second region of interest; and
displaying one or more partial images from the original image, each of the one or more partial images corresponding to one second region of interest of the one or more second regions.

15. The non-transitory computer-readable medium of claim 14, when executed by the processor, perform the processes including:
generating one or more target indices corresponding to image information corresponding to the one or more second regions of interest respectively; and
displaying the one or more target indices.

* * * * *